United States Patent [19]

Kanada et al.

[11] 4,154,818

[45] May 15, 1979

[54] GEL PRODUCT FOR DESTROYING HARMFUL MARINE ORGANISMS AND METHOD OF APPLYING THE SAME

[75] Inventors: Sadaoki Kanada, Ibaragi; Kunio Nishmura, Takatsuki; Toru Yasunaga, Osaka; Sakae Katayama, Kobe, all of Japan

[73] Assignee: Katayama Chemical Works Co., Ltd., Osaka, Japan

[21] Appl. No.: 804,933

[22] Filed: Jun. 9, 1977

[51] Int. Cl.$^2$ .................. A61K 31/74; A01N 9/00
[52] U.S. Cl. ........................... 424/81; 424/19; 424/78; 424/246; 424/270; 424/288; 424/300; 424/328; 106/15.05
[58] Field of Search ............... 424/78, 81, 288, 37, 424/328, 300, 167, 246, 270, 16, 19, 14; 106/15 R

[56] References Cited

U.S. PATENT DOCUMENTS

| | | | |
|---|---|---|---|
| 2,599,373 | 6/1952 | Chrzanowski | 424/167 |
| 3,513,234 | 5/1970 | Traber | 106/15 AF |
| 3,575,123 | 4/1971 | Shepherd et al. | 106/15 AF |
| 3,684,752 | 8/1972 | Goto et al. | 424/288 |
| 3,876,761 | 4/1975 | Shepherd | 424/81 |
| 4,010,141 | 3/1977 | Onozuka et al. | 424/288 |
| 4,053,627 | 10/1977 | Scher | 424/278 |

FOREIGN PATENT DOCUMENTS 12239  1975  Japan.

*Primary Examiner*—V. D. Turner
*Attorney, Agent, or Firm*—Hubbell, Cohen, Stiefel & Gross

[57] ABSTRACT

New gel product for exterminating harmful marine organisms. Comprises (a) about 1 to 25% by weight of a natural high molecular weight compound capable of forming a gel in water, (b) about 5 to 30% by weight of an agent for exterminating harmful marine organisms, (c) about 1 to 25% by weight of at least one compound selected from the group consisting of a water soluble synthetic linear polymer, an inorganic substance, a surfactant, an organic solvent, a gel-modifier, and mixtures thereof, and (d) water.

21 Claims, No Drawings

GEL PRODUCT FOR DESTROYING HARMFUL MARINE ORGANISMS AND METHOD OF APPLYING THE SAME

BACKGROUND OF THE INVENTION

1. Field of the Invention

This invention relates to a new gel product for exterminating harmful marine organisms and to a method of exterminating said organisms. According to the present invention, there is provided a novel gel product for exterminating harmful marine organisms, as well as a method of applying such product, which is particularly effective in preventing the boring of lumber by Teredos when the lumber is stored in a lumber pooling area in the sea.

2. Description of the Prior Art

Various exterminatory materials for destroying harmful marine organisms such as Teredos, Mytilus edulis, barnacles, Hydrozoa, Bryozoa, etc., are known. They have been applied, for example, by dissolving or suspending the active material in a solvent which is then added to the sea water so as to maintain a constant concentration.

In Japanese Patent Early Publication No. 12239/1975, there is disclosed that a copper or lead compound may be gelled with a hydrophilic synthetic resin such as a polyvinyl alcohol having a molecular weight of 500 to 3000, and such gel is used for exterminating starfish.

Among the harmful marine organisms, Teredo (commonly called shipworm or pileworm) belongs to the Teredinidae family, Bivalvia class, Mollusca. The Teredo has a way of life which is very different from other marine organisms (such as Mytilus edulis, barnacles, Hydrozoa, Bryozoan, etc.). The Teredo is a living organism which attaches to marine constructions, typically on the surface of lumber, and through metamorphosis bores into the lumber. It does not live by eating plankton in the sea water as its primary food, but rather relies upon cellulose in lumber as a nutritive source.

A floating larva of Teredo has the same way of life as one of the Bivalves, but it effects a different metamorphosis from the larvae of other Bivalves in the stage of metamorphosis after attaching, and cannot live without lumber of some other source of cellulose.

There are many occasions which require one to store lumber in the sea. The Teredo will often bore lumber during its sea storage, which, of course, markedly decreases the price. However, exterminatory products for destroying the Teredo have not heretofore been satisfactory in a lumber pool, because of a number of different problems depending upon the large surface of the sea, the particular kind of reagent, the method of application of the reagent, the effect of the reagent, etc.

It is very difficult to maintain a desired concentration of an effective component, when the component is diluted with solvents and added to the sea. Moreover, the description given in Japanese Patent Early Publication No. 12239/1975 does not result in a satisfactory gel product, nor does it result in an adequately effective exterminatory product.

The following considerations are desirable in order to obtain a satisfactory gel product:

(1) The effective (active) components should be dissolved in the sea;
(2) the amount dissolved should reach an effective concentration in a relatively short time;
(3) when the product is used in a lumber pool, the amount dissolving should be maintained at a constant rate, because the effective concentration should remain constant during the period of time which is generally required for storing lumber in sea water typically from one half to three months;
(4) the product should be able to be handled easily, that is, it should hold exhibit elasticity and flexibility, and should not be sticky on its surface;
(5) the product should float on the sea (when used in a lumber pool);
(6) if possible, the components of the product should not be harmful.

SUMMARY OF THE INVENTION

The present invention provides the gel product for exterminating harmful marine organisms, comprising
(a) about 1–25 w/w % of a natural high molecular weight compound capable of forming a gel in water,
(b) about 5–30 w/w % of an agent for exterminating harmful marine organisms,
(c) about 1–25 w/w % of at least one compound selected from the group consisting of a water-soluble synthetic linear polymer, an inorganic substance, a surfactant, an organic solvent, a gel-modifier, and mixtures thereof, and
(d) water.

[Each of the above components is occasionally referred to hereinafter as (a), (b), (c) and (d).]

DESCRIPTION OF THE PREFERRED EMBODIMENTS

The natural high molecular weight compound, (a), may be gelatin, glue, starch, carboxymethylcellulose, agar, etc. Gelatin and glue are preferred.

A gel made up of water and such a natural high molecular weight compound has a relatively strong pseudo three dimensional network by hydrogen bonding, large tensile strength, high elasticity, small surface adhesion, and moderate rate of dissolution, and hence is suitable for use as the gelling agent for the gel product in accordance with this invention.

The agent for exterminating harmful marine organisms, (b), is one which is effective as a pesticide as well as in retarding the growth of Teredo, barnacles, etc. The agents are not particularly limited. However, it is preferable that the agents are those which are effective in a very small dosage and which exhibit little or no toxicity to other forms of life. Examples of desirable exterminating agents are trisubstituted tin compounds such as triphenyl tin acetate, triphenyltin hydroxide, tricyclohexyl tin hydroxide, and the like; organic sulfur compounds such as tetramethylthiuram disulfide, dialkylthiocarbamate (preferrably in the form of its sodium salt), ethylenethiuram monosulfide, ethylene-bis-dithiocarbamate (preferably in the form of its sodium salt), 3,5-dimethyl-tetrahydro-1,3,5-thiadiazine-2-thione, 5-chloro-2-methyl-4-isothiazoline-3-one, and the like.

As preferred exterminatory agents for the Teredo there may be mentioned: triphenyl tin hydroxide, ethylenethiuram monosulfide, tetramethylthiuram monosulfide, 3,5-dimethyl-tetrahydro-1,3,5-thiaziazin-2-thione, etc.

As regards item (c), i.e., at least one compound selected from the group consisting of a water-soluble synthetic linear polymer, an inorganic substance, a surfactant, an organic solvent, and a gel modifier, item (c)

is for the purpose of obtaining the desired performance of the exterminatory product. The various compounds utilized are suitably selected according to the particular purpose of application. The effects caused by adding one or more of them are as follows.

The water soluble linear polymer is added not only to control the amount of active component which dissolves in the sea, but also to provide a suitable softness for the ultimate gel product.

The water-soluble linear polymer should desirably have a molecular weight exceeding 100,000, preferably about or in excess of 1,000,000. The higher the molecular weight, the less the amount required. The following polymers are particularly suitable: acrylic and methacyrlic resins such as alkali metal polyacrylates, polyacrylamide, alkali metal polymethacrylates, poly-2-hydroxyethyl methacrylate, acrylic acid/acrylamide copolymers or their salts, acrylic acid/maleic acid copolymers or their salts; polyethylenoxide, etc.

Examples of inorganic substances are water-soluble sulfates (for example, alkali metal sulfates such as sodium sulfate), alkali metal halides (for example, sodium chloride, potassium chloride), water-soluble nitrites (for example, alkali metal nitrites such as sodium nitrite), water-soluble thiosulfates (for example, alkali metal thiosulfates such as sodium thiosulfate), talc, diatomaceous earth, etc.

These inorganic substances (with the exception of talc and diatomaceous earth) will be effective in adjusting the osmotic pressure of the gel product, so as to control diffusion of sea water into and out of the product.

If certain types of polymers such as, e.g., sodium polymethacrylate, wherein the sodium is able to be substituted by multivalent metal ions, is employed as the water-soluble synthetic linear polymer, and if the gel product of this invention is prepared in fresh water (that is, under circumstances where water-soluble inorganic substances are not present) and is then immersed in sea water, gumming will occur and the product will change to an insoluble white material, whereas the product can be penetrated by sea water when an alkali metal is present in the polymer, for example, Na is substituted by ions such as $Mg^{++}$, $Ca^{++}$, etc. Such gumming is avoided by adding the above mentioned inorganic substance.

When one or more trisubstituted tin compounds are used as the active component against harmful marine organisms, these tend to generate radicals. When such a radical reacts with the natural high molecular weight compound capable of forming the gel body, it decreases its molecular weight by terminating the molecular chain of the polymer, and tends to break down the gel. Accordingly, it is preferable to bind such generated radicals, for example, by adding a nitrite such as sodium nitrite.

The surfactant is added to decrease the specific gravity, by forming bubbles in the gel-body to impart buoyancy. The surfactant is also useful to unify the gel-body and to adjust its dissolubility. Examples of a suitable surfactant include: anionic surfactants such as a salt of a higher fatty acid, a higher alcohol sulfate, alkyl aryl sulfonates, etc.; nonionic surfactants such as polyoxyethylene alkyl ether, polyoxyethylene alkyl phenol ether, polyoxyethylene alkyl ester, sorbitan alkyl ester, polyoxyethylene sorbitan alkyl ester, polyoxyethylene alkylamine, polyoxyethylene alkylamide, poly(oxyethylene-oxypropylene) copolymer and polyoxyethylene-polyoxypropylene alkylene diamine; cationic surfactants such as alkyl trimethyl ammonium salt, alkyl dimethyl benzlammonium salt and alkylpyridinium salt; amphoteric surfactants such as alkyl betaine and alkyl imidazoline sulfonate.

The organic solvent is useful for unifying the gel-body and for adjusting its rate of dissolution. The following solvents are given by way of example: monoalcoholic solvents such as methanol, ethanol, ispropanol, etc., polyolic solvents such as ethylene gylcol, ethylene glycol-monomethyl ether, propylene glycol, etc.; nitrogen-containing solvents such as ethanolamine, dimethyl formamide, etc.

The following compounds are examples of suitable gel-modifiers: formaldehyde, para-formaldehyde, hexamethylenetetramine, etc. These compounds will react with the polymer-substances to form crosslinks and increase the heat stability. (That is, the temperature wherein the shape will not be retained because of softening and flowing, is increased.)

A preferable range is readily ascertained regarding the ratio of components of the gel-product provided by the invention.

If too small an amount of the natural high molecular weight compound, (a), is added, the product can form a low elastic and sticky gel. If too large an amount of the natural high molecular compound is added, the gel becomes hard and brittle, and the rate of dissolution of the gel become too slow. Accordingly, it is preferable to use the natural high molecular weight compound in an amount of from about 1 to 25 ww %.

If too low an amount of (b), the active component against harmful marine organisms, is added, the product does not develop its remarkable effect. If too large an amount of this component is used, its concentration in sea water becomes higher than needed for the effective concentration. This is not only uneconomical, but also disadvantageous as regards environmental pollution. Therefore, it is preferable to use the active component in an amount of from about 5 to 30 w/w %.

The component (c) is prepared so that there is present at least one compound in an amount of from about 1 to 25 w/w %, said compound being selected from the group consisting of a water-soluble synthetic linear polymer, an inorganic substance, a surfactant, an organic solvent, a gel-modifier, and mixtures thereof.

Preferable examples of amounts of each of the above compounds are as follows:

The water-soluble linear polymer will increase the softness of the gel, but if too great an amount of the linear polymer is added, the gel becomes too stickly to handle. Therefore, it is preferable to use this polymer in an amount of from about 0.5 to 5.0 w/w %.

The inorganic substance will decrease the tensile strength of the gel if too great an amount is added. Therefore it is preferable to use this substance in an amount of from about 1.0 to 10.0 w/w %.

The surfactant may cause too many bubbles and result in a bulk specific gravity that is too low, if too large an amount of surfactant is added. This results in a decrease in the tensile strength of the gel. Therefore, it is preferable to use the surfactant in an amount of from about 0.1–5.0 w/w %.

The organic solvent may cause the rate of dissolution of the gel to become too great, if too large an amount is added. Therefore, it is preferable to use this solvent in an amount of from about 1.0 to 20.0 w/w %.

The gel-modifier will cause the gel to harden, to become brittle, and will lower the dissolution rate, if too large an amount is added. Therefore, it is preferable to use this modifier in an amount of from about 0.01 to 5.0 w/w %.

These components in (c) are added to improve the mechanical properties of the gel (elasticity, softness, and stickiness), to adjust the dissolution rate (the initial and stationary dissolution rates hereinafter referred to), to uniformly mix both of gel-modifier and other components, to adjust the osmotic pressure, to bind free radicals (upon the addition of a trisubstituted tin compound), to adjust the bulk specific gravity (as regards the amount of bubbles), and to increase the heat stability (to prevent softening and flowing even upon a rise in temperature). The types and quantitities of these components in (c) are according to the purpose of their application.

The following combinations and ranges are preferred.

(I)
(a) 1 to 25 w/w %
(b) 5 to 30 w/w/ %
(c) Water-soluble linear polymer, 0.5 to 5.0 w/w %
(d) the remainder—water (II)
(a) 1 to 25 w/w %
(b) 5 to 30 w/w %
(c) Water-soluble synthetic linear polymer, 0.5 to 5.0 w/w % Inorganic substance, 1 to 10.0 w/w % Surfactant, 0.1 to 5.0 w/w % Total of the components in (c) 1 to 25 w/w %
(d) the remainder—water (III)
(a) 1 to 25 w/w %
(b) 5 to 30 w/w %
(c) Water-soluble synthetic linear polymer, 0.5 to 5.0 w/w % Inorganic substance, 1.0 to 10.0 w/w % Surfactant, 0.1 to 5.0 w/w % Organic solvent, 1.0 to 20.0 w/w % Total of the components in (c), 1 to 25 w/w %
(d) the remainder—water (IV)
(a) 1 to 25 w/w %
(b) 5 to 30 w/w %
(c) Water-soluble synthetic linear polymer, 0.5 to 5.0 w/w % Inorganic substance, 1.0 to 10.0 w/w % Surfactant, 0.1 to 5.0 w/w % Organic solvent, 1.0 to 20.0 w/w % Gel-modifier, 0.01 to 5.0 w/w % Total of the components in (c), 1 to 25 w/w %
(d) the remainder—water (V)
(a) 1 to 25 w/w %
(b) 5 to 30 w/w %
(c) Water-soluble synthetic linear polymer, 0.5 to 5.0 w/w % Organic solvent, 1.0 to 20.0 w/w % Total of the components in (c), 1 to 25 w/w %
(d) the remainder—water (VI)
(a) 1 to 25 w/w %
(b) 5 to 30 w/w %
(c) Water-soluble synthetic linear polymer, 0.5 to 5.0 w/w % Inorganic substance, 1.0 to 10.0 w/w % Gel-modifier, 0.01 to 5.0 w/w % Total of the components in (c), 1 to 25 w/w %
(d) the remainder—water (VII)
(a) 1 to 25 w/w %
(b) 5 to 30 w/w %
(c) Inorganic substance, 1.0 to 10.0 w/w %
(d) the remainder—water (VIII)
(a) 1 to 25 w/w %
(b) 5 to 30 w/w %
(c) Inorganic substance, 1.0 to 10.0 w/w % Surfactant, 0.1 to 5.0 w/w % Total of the components in (c), 1 to 25 w/w %
(d) the remainder—water It is to be noted that although it is desirable that, apart from elements (a), (b), and (c), the remainder, element (d), be water, this is not essential. Thus, in addition to water, other components may also be present provided they do not exert too serious an adverse effect upon the properties and performance of the gel product of this invention.

In order to prepare the gel product for exterminating harmful marine organisms according to this invention, the natural high molecular weight compound capable of forming a gel is dissolved or suspended in cold or warm water. This solution or suspension is added to a previously prepared mixture of the exterminating agent and one or more compounds selected from the group consisting of water-soluble synthetic linear polymer, surfactant, organic solvent, gel-modifier, and mixtures thereof, and then is thoroughly mixed. The gelled product is prepared by pouring this mixture into a suitable mold.

Alternatively, the exterminatory agent is mixed with one or more compounds selected from the water-soluble synthetic linear polymer, surfactant, organic solvent, gel-modifier, and mixtures thereof. The gel product may be prepared by adding the above mixture to a previously prepared solution or suspension by dissolving or suspending the natural high molecular weight compound in cold or hot water.

The shape of the gelled product of this invention may take any form, e.g., a cylinder, sphere, cube, or plate. The mold is selected so as to obtain the shape of gel desired. When, e.g., a gel in the form of a column is desired, it is preferable that it have a size of 40 mm to 100 mm in diameter and 40 mm to 100 mm in length. When a sphere or cube preparation is desired, it preferably should have a weight of from about 1 to 5 kgs.

In order to prevent boring of lumber in the sea by the Teredo, such a type of the gel product is immersed into a lumber pool in the sea, as by putting it into a net, a basket, or a perforated vinyl bag. The extermination of the Teredo is carried out by suspending such gel products at appropriate places between rafts in a lumber pool, or by inserting them into the raft itself. An effective concentration of the exterminatory product for Teredo generally is extremely dilute, such as 1 to 100 ppb (parts per billion). At such concentrations the metamorphosis of the Teredo from the larva to the imago will be prevented. There is no problem as regards environmental pollution, because of the very dilute concentration used. Further, when the gel product of this invention is employed, its effective concentration will be maintained over a period of two or three months. Hence, it is also very economical to use this gel product, because the extermination is carried out over a long period.

The gel product may be also applied to prevent the growth of Mytilus edulis, barnacles, and/or Hydrozoa, which tend to adhere on walls and other surfaces in systems where sea water is used as the cooling water.

That is, the gel product which contains an ingredient active for inhibiting the growth of such marine organisms, e.g., sodium dithiocarbamate or tetramethylthiuram disulfide, is shaped as a cylinder or plate, which may be put into a wire mesh basket, and then is suspended, by supporting means, at the inlet of the sea water to the system.

The following examples will further illustrate the invention.

EXAMPLE I

The products were formulated using the following components in the amounts stated:

| | | | |
|---|---|---|---|
| (1) | Gelatin (JIS, fourth grade) | 10 | (w/w %) |
| | Triphenyltin hydroxide | 10 | |
| | Sodium polyacrylate (MW = about 3,000,000) | 2 | |
| | Sodium nitrite | 1 | |
| | Water | 77 | |
| (2) | Glue (JIS, third grade) | 10 | |
| | Ethylenethiuram monosulfide | 15 | |
| | Polyethylene oxide (MW = about 2,000,000) | 3 | |
| | Talc | 5 | |
| | Water | 67 | |
| (3) | Glue (JIS, third grade) | 4 | |
| | Tetramethylthiuram disulfide | 20 | |
| | Triphenyltin hydroxide | 2 | |
| | 3,5-dimethyl-tetrahydro-1,-thiadiazine-2-thione | 0.5 | |
| | Sodium polyacrylate (MW = about 8,000,000) | 2.5 | |
| | Sodium borate | 3 | |
| | Sodium chloride | 3 | |
| | Sodium nitrite | 1 | |
| | Water | 64 | |
| (4) | Gelatin (JIS, fourth grade) | 6 | |
| | Stach (potato) | 2 | |
| | Tetramethylthiuram disulfide | 20 | |
| | Polyacrylamide (MW = about 8,000,000) | 2 | |
| | Glycerin | 3 | |
| | Water | 67 | |
| (5) | Glue (JIS, third grade) | 8 | |
| | CMC (carboxymethyl cellulose) (MW = about 30,000) | 2 | |
| | Ethylenethiuram monosulfide | 20 | |
| | Polyoxyethylene lauryl ether (HLB, 13) | 3 | |
| | Sodium borate | 2 | |
| | Water | 65 | |
| (6) | Gelatin (JIS, fourth grade) | 2 | |
| | Glue (JIS, third grade) | 4 | |
| | Tetramethylthiuram disulfide | 25 | |
| | Sodium polyacrylate (MW = about 8,000,000) | 1 | |
| | Polyacrylamide (MW = about 8,000,000) | 1 | |
| | Sodium chloride | 2 | |
| | Polyoxyethylene palmalkylamide | 1.9 | |
| | Formalin (37% by weight) | 0.1 | |
| | Water | 63 | |

Gelled cylinders of a diameter about 5 cm and a length about 50 cm (weight about 1 kg) were made for each of the products (1) to (6) referred to above, and were cut into pieces having a length of about 5 cm (about 100 g). A piece was then put in a plastic net bag and immersed in 25 liters of natural sea water which was maintained at a temperature 20°±2° C. in a 30 liter vat and was stirred by using a motor with reduction gear to cause continuous flow. The sea water was renewed once every three days. The amount of dissolved material per day was estimated by weighing the piece after 5, 30, and 60 days. In addition, the flow temperature of each of the gel columns was measured. The data are given below.

| Example of Product No. | Weight of the dissolved material (g/day) | | | Flow temperature* (°C.) |
|---|---|---|---|---|
| | after 5 days | after 30 days | after 60 days | |
| (1) | 1.2 | 1.5 | 1.2 | 30 to 32 |
| (2) | 2.2 | 2.3 | all dissolved away | 28 to 30 |
| (3) | 2.1 | 1.6 | 1.4 | over 60 |
| (4) | 2.2 | 2.2 | all dissolved away | 30 to 32 |
| (5) | 2.3 | 2.6 | all dissolved away | 38 to 30 |
| (6) | 2.1 | 1.7 | 1.5 | over 60 |

*The temperature at which the product commenced losing its shape (dimensional stability) by softening and flowing.

EXAMPLE II

Gel test cylinders were made as described in Product (1) of Example I.

One cylinder (2 kg), length 100 cm, was put in a plastic net bag. The formulation was as follows:

| | |
|---|---|
| Triphenyl tin hydroxide | 200 g |
| Sodium polyacrylate (MW = about 8,000,000) | 40 g |
| Gelatin (fourth grade) | 200 g |
| Sodium nitrite | 20 g |
| Water | 1,540 g |

Gel cylinders of the above type were inserted into rafts beneath their construction. That is, 30 rafts, length 4 m (a bundle of 50 pieces of lumber of lengths 4 m) were divided into 5 groups, and in each, ½, 1, 2, 3, 4 or 5 gel cylinders were inserted. All groups were enclosed by large lauan lumbers so as to control the flow of sea water as much as possible. Then test panels (Tsuga Heterophylla Sargent 20 cm×5 cm×2 cm) were suspended at 4 places around each of these groups, so as to judge the effect of the product, and were taken out periodically.

The effect was observed by taking X-ray photographs. The test was continued for two months (June 23 to August 23).

The average residual amount of the said product was 20 to 25% after two months. The results are given in Table I.

TABLE I

| Period | | Number of holes bored | 30 days Number of worms over 10mm long | Length of longest worm(mm) | Number of holes bored | 60 days Number of worms over 10mm long | Length of longest worm (mm) |
|---|---|---|---|---|---|---|---|
| Control group | A | 6 | 0 | 6 | 43 | 11 | 50 |
| | B | 5 | 0 | 4 | 40 | 16 | 57 |
| | C | 9 | 0 | 6 | 27 | 23 | 82 |

TABLE I-continued

| Period | | Number of holes bored (30 days) | Number of worms over 10mm long (30 days) | Length of longest worm(mm) (30 days) | Number of holes bored (60 days) | Number of worms over 10mm long (60 days) | Length of longest worm (mm) (60 days) |
|---|---|---|---|---|---|---|---|
| | D | 8 | 0 | 2 | 33 | 18 | 94 |
| Test group ½ cylinder inserted | 1 | 2 | 0 | 1 | 6 | 4 | 23 |
| | 2 | 3 | 0 | 1 | 5 | 3 | 20 |
| | 3 | 0 | 0 | 0 | 9 | 1 | 11 |
| | 4 | 0 | 0 | 0 | 5 | 0 | 9 |
| Test group 1 cylinder inserted | 5 | 1 | 0 | 1 | 8 | 3 | 16 |
| | 6 | 0 | 0 | 0 | 4 | 1 | 27 |
| | 7 | 1 | 0 | 1 | 2 | 0 | 6 |
| | 8 | 0 | 0 | 0 | 5 | 0 | 6 |
| Test group 2 cylinders inserted | 9 | 1 | 0 | 1 | 7 | 2 | 15 |
| | 10 | 2 | 0 | 2 | 9 | 3 | 25 |
| | 11 | 0 | 0 | 0 | 1 | 0 | 9 |
| | 12 | 2 | 0 | 1 | 8 | 2 | 15 |
| Test group 3 cylinders inserted | 13 | 0 | 0 | 0 | 4 | 2 | 14 |
| | 14 | 0 | 0 | 0 | 4 | 2 | 11 |
| | 15 | 2 | 0 | 2 | 9 | 0 | 9 |
| | 16 | 1 | 0 | 1 | 14 | 0 | 9 |
| Test group 4 cylinders inserted | 17 | 0 | 0 | 0 | 5 | 1 | 10 |
| | 18 | 0 | 0 | 0 | 2 | 1 | 11 |
| | 19 | 3 | 0 | 1 | 8 | 2 | 18 |
| | 20 | 2 | 0 | 1 | 11 | 0 | 9 |
| Test group 5 cylinders inserted | 21 | 1 | 0 | 1 | 3 | 0 | 3 |
| | 22 | 2 | 0 | 2 | 5 | 2 | 20 |
| | 23 | 0 | 0 | 0 | 8 | 0 | 8 |
| | 24 | 0 | 0 | 0 | 10 | 1 | 14 |

EXAMPLE III

A gel test cylinder was made according to Product (3) of Example I.

One cylinder (1 kg), length 50 cm, was put in a plastic net bag. The formulation was as follows:

| | |
|---|---|
| Tetramethylthiuram disulfide | 200 g |
| Triphenyltin hydroxide | 20 g |
| Sodium polyacrylate (MW = about 8,000,000) | 25 g |
| Gelatin (JIS, fourth grade) | 40 g |
| 3,5-dimethyl-tetrahydro-1,3,5-thiadiazine-2-thione | 5 g |
| Sodium borate | 30 g |
| Sodium chloride | 30 g |
| Sodium nitrite | 10 g |
| Water | 640 g |

Gel cylinders of the above type were inserted into rafts beneath this construction. That is, one or two cylinders were inserted into 58 rafts of length 4 m (a bundle of 50 pieces of lumber of length 4 m) and into 21 rafts of length 8 m (a bundle of 50 pieces of lumber of length 8 m) respectively. These rafts were lined up in four groups on the surface of a lumber pool (about 60 m×20 m). Then the above gel cylinders were suspended, one by one, at intervals of 3 m around the outside rafts lined up. Test panels (Tsuga Heterophylla Sargent 20 cm×50 cm×2 cm) were suspended, one by one, at intervals of 8 to 10 meters around the outside rafts and between them, and were taken out periodically. This testing was continued for two months (October 13 to December 13). The average residual amount of the product was 15 to 20% after two months. The results are given in Table II.

TABLE II

| Period | | Number of holes bored (30 days) | Number of worms over 10mm long (30 days) | Length of longest worm(mm) (30 days) | Number of holes bored (60 days) | Number of worms over 10mm long (60 days) | Length of longest worms(mm) (60 days) |
|---|---|---|---|---|---|---|---|
| Control Group | A | 13 | 0 | 4 | 17 | 8 | 14 |
| | B | 10 | 0 | 3 | 15 | 8 | 23 |
| | C | 8 | 0 | 5 | 16 | 2 | 18 |
| | D | 14 | 0 | 3 | 14 | 4 | 16 |
| Test Group | 1 | 0 | 0 | 0 | 4 | 0 | 6 |
| | 2 | 0 | 0 | 0 | 3 | 0 | 2 |
| | 3 | 0 | 0 | 0 | 4 | 0 | 7 |
| | 4 | 3 | 0 | 1 | 5 | 0 | 6 |
| | 5 | 0 | 0 | 0 | 0 | 0 | 0 |
| | 6 | 1 | 0 | 1 | 2 | 0 | 3 |
| | 7 | 2 | 0 | 1 | 2 | 0 | 8 |
| | 8 | 1 | 0 | 1 | 2 | 0 | 3 |
| | 9 | 0 | 0 | 0 | 2 | 0 | 2 |
| | 10 | 0 | 0 | 0 | 6 | 0 | 1 |
| | 11 | 0 | 0 | 0 | 5 | 0 | 7 |

TABLE II-continued

| Period | 30 days | | | 60 days | | |
|---|---|---|---|---|---|---|
| | Number of holes bored | Number of worms over 10mm long | Length of longest worm(mm) | Number of holes bored | Number of worms over 10mm long | Length of longest worms(mm) |
| 12 | 0 | 0 | 0 | 3 | 0 | 6 |
| 13 | 0 | 0 | 0 | 2 | 0 | 2 |
| 14 | 0 | 0 | 0 | 3 | 0 | 6 |
| 15 | 2 | 0 | 3 | 3 | 0 | 5 |
| 16 | 2 | 0 | 1 | 3 | 0 | 4 |
| 17 | 1 | 0 | 1 | 4 | 0 | 8 |
| 18 | 2 | 0 | 1 | 3 | 0 | 4 |
| 19 | 1 | 0 | 1 | 1 | 0 | 4 |
| 20 | 2 | 0 | 1 | 3 | 0 | 4 |
| 21 | 0 | 0 | 0 | 0 | 0 | 0 |
| 22 | 2 | 0 | 2 | 3 | 0 | 3 |
| 23 | 1 | 0 | 1 | 4 | 0 | 5 |
| 24 | 0 | 0 | 0 | 2 | 0 | 2 |
| 25 | 1 | 0 | 1 | 1 | 0 | 4 |

Variations can, of course, be made without departing from the spirit and scope of the invention.

Having thus described the invention, what is desired to be secured by Letters Patent and hereby claimed is:

1. A gel product for exterminating or inhibiting harmful marine organisms from boring or attaching to lumber stored in salt water when said gel product is disposed in salt water proximate to said lumber, said gel product comprising
   (a) from about 1 to 25% by weight of a natural, high molecular weight compound capable of forming a gel in water, said compound being gelatin, glue, starch, carboxymethyl cellulose or agar;
   (b) from about 5 to 30% by weight of an agent capable of exterminating harmful marine organisms;
   (c) from about 1 to 25% by weight of a compound selected from the group consisting of a water-soluble synthetic linear polymer, an inorganic material, a surfactant, an organic solvent, a gel-modifier, and mixtures thereof, wherein the water-soluble synthetic linear polymer is a polyacrylate, polyacrylamide, polyethyleneoxide, a polymethacrylate, acrylic acid/maleic acid copolymer or a salt thereof, acrylic acid/acrylamide copolymer or salt thereof, and wherein the inorganic material is a water-soluble sulfate, an alkali metal halide, a water-soluble borate, a water-soluble nitrite, a water-soluble thiosulfate, talc or diatomaceous earth; and
   (d) water; said gel product exhibiting elasticity and flexibility.

2. The product of claim 1, wherein the exterminating agent is triphenyltin hydroxide, triphenyltin acetate, tricyclohexyltin hydroxide, tetramethylthiuram disulfide, ethylenethiuram monosulfide, ethylenebis-dithiocarbamate, 3,5-dimethyltetrahydro-1,3,5-thiadiazine-2-thione, or 5-chloro-2-methyl-4-isothiazoline-3-one.

3. The product of claim 1, wherein element (c) comprises a water-soluble linear polymer present in an amount of from about 0.5 to 5% by weight.

4. The product of claim 3, additionally containing from about 1 to 10% by weight of said inorganic material and from about 0.1 to 5.0% by weight of said surfactant.

5. The product of claim 4, additionally containing from about 1 to 20% by weight of said organic solvent.

6. The product of claim 5, additionally containing from about 0.01 to 5.0% by weight of said gel-modifier.

7. The product of claim 3, additionally containing from about 1 to 20% by weight of said organic solvent.

8. The product of claim 1, wherein element (c) comprises said inorganic material in an amount of from about 1.0 to 10.0% by weight.

9. The product of claim 1, additionally containing from about 0.1 to 5.0% by weight of said surfactant.

10. The product of claim 1, said product containing about 10% by weight of gelatin, about 10% by weight of triphenyltin hydroxide, about 2% by weight of sodium polyacrylate, about 1% by weight of sodium nitrite, and about 77% by weight of water.

11. The product of claim 1, said product containing about 10% by weight of glue, about 15% by weight of ethylenethiuram monosulfide, about 3% by weight of polyethyleneoxide, about 5% by weight of talc, and about 67% by weight of water.

12. The product of claim 1, said product containing 4% by weight of glue, about 20% by weight of tetramethylthiuram disulfide, about 2% by weight of triphenyltin hydroxide, about 0.5% by weight of 3,5-dimethyltetrahydro-1,3,5-thiadiazin-2-thione, about 2.5% by weight of sodium polyacrylate, about 3% by weight of sodium borate, about 3% by weight of sodium chloride, about 3% by weight of sodium nitrite, and about 64% by weight of water.

13. The product of claim 1, said product containing about 6% by weight of gelatin, about 2% by weight of starch, about 20% by weight of tetramethylthiuram disulfide, about 2% by weight of polyacrylamide, about 3% by weight of glycerin, and about 67% by weight of water.

14. The product of claim 1, said product containing about 8% by weight of glue, about 20% by weight of ethylenethiuram monosulfide, about 2% by weight of carboxymethylcellulose, about 2% by weight of sodium borate, about 3% by weight of polyoxyethylene lauryl ether, and about 65% by weight of water.

15. The product of claim 1, said product containing about 2% by weight of gelatin, about 4% by weight of glue, about 25% by weight of tetramethylthiuram disulfide, about 1% by weight of sodium polyacrylate, about 1% by weight of polyacrylamide, about 2% by weight of sodium chloride, about 1.9% by weight of polyoxyethylene palmalkylamide, about 0.1% by weight of formalin, and about 63% by weight of water.

16. The product of claim 1, wherein the remainder of said product, apart from elements (a), (b), and (c), is water.

17. A method of inhibiting harmful marine organisms from boring or attaching to lumber stored in salt water, this method comprising disposing the gel product of claim 1 in said salt water and proximate to said lumber.

18. The product of claim 1, wherein element (c) comprises said water-soluble synthetic linear polymer in an amount of from 0.5 to 5% by weight, said inorganic material in an amount of from about 1 to 10% by weight, and said gel-modifier in an amount of from about 0.01 to 5% by weight.

19. The product of claim 1, wherein element (c) comprises said inorganic material in an amount of from about 1 to 10% by weight and said surfactant in an amount of from about 0.1 to 5% by weight.

20. The product of claim 3, additionally containing from 1 to 10% by weight of said inorganic material.

21. The product of claim 18, additionally containing from 0.1 to 10% by weight of said surfuctant.